United States Patent [19]

Wolf et al.

[11] Patent Number: 5,741,947

[45] Date of Patent: Apr. 21, 1998

[54] PREPARATION OF ALKOXYLATION PRODUCTS IN THE PRESENCE OF MIXED HYDROXIDES MODIFIED WITH ADDITIVES

[75] Inventors: Gerhard Wolf, Ketsch; Bernd Burkhart, Mutterstadt; Guenter Lauth, Grosskarlbach; Horst Trapp, Plankstadt; Alfred Oftring, Bad Duerkheim, all of Germany

[73] Assignee: BASF Aktiengesellschaft, Ludwigshafen, Germany

[21] Appl. No.: 586,803

[22] PCT Filed: Jul. 5, 1994

[86] PCT No.: PCT/EP94/02195

§ 371 Date: Jan. 29, 1996

§ 102(e) Date: Jan. 29, 1996

[87] PCT Pub. No.: WO95/04024

PCT Pub. Date: Feb. 9, 1995

[30] Foreign Application Priority Data

Jul. 28, 1993 [DE] Germany .............. 43 25 237.0

[51] Int. Cl.[6] .................................. C07C 43/11
[52] U.S. Cl. .............. 568/618; 502/341; 556/28; 554/149
[58] Field of Search ............. 568/618; 502/341; 556/28; 554/149

[56] References Cited

U.S. PATENT DOCUMENTS 4,774,212   9/1988   Drezdon ................... 502/62

FOREIGN PATENT DOCUMENTS

| 4010606 | 4/1990 | Germany . |
| 4034305 | 10/1990 | Germany . |
| 40 02 988 | 8/1991 | Germany . |
| 41 06 404 | 7/1992 | Germany . |
| 9220619 | 5/1992 | WIPO . |

OTHER PUBLICATIONS

P.K. Dutta and M. Puri, J. Phys. Chem., 1989, 93,376–381.
K. Chibwe and W. Jones, J. Chem. Commun. 1989, 926–927.
K. Chibwe and W. Jones, Prep. Am. Chem. Soc. 34 (1989) 507–510.

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

Alkoxylation products are prepared by reacting compounds having active hydrogen atoms with $C_2$–$C_4$-alkylene oxides in the presence of a mixed hydroxide built up of polycations and modified with additives and having the general formula I or II $$[M(II)_{1-x}M(III)_x(OH)_2]A_{x/n} \cdot m\, L \qquad (I)$$

$$[LiAl_2(OH)_6]A_{1/n} \cdot m\, L \qquad (II)$$

where

M(II) is at least one divalent metal ion,

M(III) is at least one trivalent metal ion,

A is at least one inorganic anion and

L is an organic solvent or water, n is the valence of the inorganic anion A or in the case of a plurality of anions A is their mean valence and x can assume a value of from 0.1 to 0.5 and m can assume a value of from 0 to 10, as alkoxylation catalyst, wherein the mixed hydroxide contains additives.

11 Claims, No Drawings

PREPARATION OF ALKOXYLATION PRODUCTS IN THE PRESENCE OF MIXED HYDROXIDES MODIFIED WITH ADDITIVES

This is the U.S. National Stage Application of PCT/EP/94/02195 filed Jul. 5, 1994 now WO95/04024 published Feb. 9, 1995.

The present invention relates to an improved process for preparing alkoxylation products by reacting compounds having active hydrogen atoms with $C_2$–$C_4$-alkylene oxides in the presence of a mixed hydroxide built up of polycations and modified with certain additives as alkoxylation catalyst. Since some of these mixed hydroxides are new compounds, the invention further relates to these new mixed hydroxides and processes for their preparation.

Alkoxylation products having a narrow molecular weight distribution or homologue distribution, known as "narrow cut", "narrow range" or "peaked" alkoxylates, are becoming increasingly important since they have improved use properties in comparison with normal alkoxylates having a broad distribution, and are conventionally prepared using alkali metal hydroxides or boron trifluoride adducts as catalysts. They are mainly used as surfactants in detergents, cleaning compositions and personal care compositions, but also in the paper and textile fibers industry. Efficient synthetic routes to such narrow cut alkoxylates are therefore urgently sought.

DE-A 40 10 606 (1) relates to the use of hydrotalcites hydrophobicized with anions of an aliphatic $C_4$–$C_{44}$-dicarboxylic acid or an aliphatic $C_2$–$C_{34}$-monocarboxylic acid as ethoxylation or propoxylation catalysts for compounds having active hydrogen atoms or for fatty acid esters. The alkoxylation products obtained using these catalysts have a narrow homologue distribution.

DE-A 40 34 305 (2) discloses double-layer hydroxide compounds containing magnesium, zinc, calcium, iron, cobalt, copper, cadmium, nickel or manganese as divalent metal and aluminum, iron, chromium, manganese, bismuth or cerium as trivalent metal and carbonate, hydrogencarbonate, sulfate, nitrate, nitrite, phosphate, hydroxide or halide as inorganic anion in addition to hydroxide and hydrophobicized with anions of an aliphatic $C_4$–$C_{44}$-dicarboxylic acid or an aliphatic $C_2$–$C_{34}$-monocarboxylic acid. These compounds are recommended as alkoxylation catalysts for compounds having active hydrogen atoms or fatty acid esters.

WO-A 92/11224 (3) relates to an alkoxylation process for alcohols to give glycol ethers using an anionic double-hydroxide clay such as hydrotalcite having an essentially intact layer structure as alkoxylation catalyst, which clay contains anions of the alcohol being reacted built in between the layers. Alcohols specified for this purpose are aliphatic, cycloaliphatic or aromatic alcohols, preferably having up to 8 carbon atoms, eg. methanol, ethanol, cyclohexanol or phenol.

However, the specified alkoxylation catalysts still have a series of deficiencies. In particular, the content of polyalkylene glycol formed as by-product in the alkoxylation and of unalkoxylated starting compound are still too high. The molecular weight distribution is likewise still too broad.

It is an object of the present invention to provide alkoxylation catalysts which can be prepared more efficiently and at the same time simply and economically and which no longer have the abovementioned deficiencies.

We have found that this object is achieved by a process for preparing alkoxylation products by reacting compounds having active hydrogen atoms with $C_2$–$C_4$-alkylene oxides in the presence of a mixed hydroxide built up of polycations and modified with additives and having the general formula I or II

where

M(II) is at least one divalent metal ion,

M(III) is at least one trivalent metal ion,

A is at least one inorganic anion and

L is an organic solvent or water, n is the valence of the inorganic anion A or in the case of a plurality of anions A is their mean valence and x can assume a value of from 0.1 to 0.5 and m can assume a value of from 0 to 10, as alkoxylation catalyst, wherein the mixed hydroxide contains as additives (a) aromatic or heteroaromatic mono- or polycarboxylic acids or their salts, (b) aliphatic mono- or polycarboxylic acids or their salts having an isocyclic or heterocyclic ring in the side chain, (c) monoesters of dicarboxylic acids or their salts, (d) carboxylic anhydrides, (e) aliphatic or aromatic sulfonic acids or their salts, (f) $C_8$–$C_{18}$-alkyl sulfates, (g) long-chain paraffins, (h) polyetherols or polyether polyols or (j) alcohols or phenols, which are not built in between the layers of the mixed hydroxide I or II.

Suitable divalent metal ions M(II) are, in particular, zinc, calcium, strontium, barium, iron, cobalt, nickel, cadmium, manganese, copper and especially magnesium.

Suitable trivalent metal ions M(III) are, in particular, iron, chromium, manganese, bismuth, cerium and especially aluminum.

Suitable inorganic anions A are, in particular, hydrogencarbonate, sulfate, nitrate, nitrite, phosphate, chloride, bromide, fluoride, hydroxide and especially carbonate.

The valence or the mean valence n of the inorganic anion(s) A is normally in the range from 1 to 3.

L is an organic solvent, in particular an alcohol such as methanol, ethanol or isopropanol, or especially water.

A large number of mixed hydroxides comprising divalent and trivalent metals and built up of polycations is known. Also known are such mixed hydroxides comprising monovalent and trivalent metals ("lithium aluminates", see general formula II). The majority of these compounds has a layer structure (typical representative: hydrotalcite), but mixed hydroxides having a different structure are also known.

For mixed hydroxides having a layer structure, the literature gives a number of synonymous names, eg. "Anionische Tone", "Anionic clays", "Hydrotalkit-ähnliche Verbindungen", "Layered double hydroxides (=LDHs)", "Feitknechtverbindungen" or "Doppelschichtstrukturen".

The class of mixed hydroxides having a layer structure is comprehensively described in the review articles by Cavani et al. or Allmann (F. Cavani, F. Trifirò and A. Vaccari, "Hydrotalcite-type anionic clays: preparation, properties and applications", Catalysis Today, 11 (1991) 173–301; R. Allmann, "Doppelschichtstrukturen mit brucitähnlichen Schichtionen", Chimia 24 (1970) 99–108).

Examples of mixed hydroxides built up of polycations and not having a layer structure are the ettringites. These compounds were described by Feitknecht et al., their structure was determined by Moore et al. (W. Feitknecht und H.W. Buser, "Zur Kenntnis der nadeligen Calcium-Aluminumhydroxysalze", Helv. Chim. Acta 32 (1949) 2298–2305; A. E. Moore und H. F. Taylor, "Crystal structure of ettringite", Acta Cryst. B 26 (1970) 386–393).

Characteristic of all mixed hydroxides used according to the present invention is a structure comprising positively charged mixed hydroxide units (polycations) between which anions are located to balance the charge. In addition to the anions A, solvent molecules L are generally also located between the positively charged units. These polycations are generally layers, but can also, eg. in the case of ettringite, assume other shapes. The anions between the polycations can generally be exchanged.

The structure of the mixed hydroxides, particularly the distance of the polycations from one another, can be determined by X-ray diffraction. The distances of the polycations from one another, eg. the layer spacings in hydrotalcite, depend mainly on the nature of the anions A and can be from about 4 Å to about 45 Å.

An important representative of mixed hydroxides having a layer structure is hydrotalcite. Naturally occurring hydrotalcite has the chemical composition $[Mg_6Al_2(OH)_{16}]CO_3 \cdot 4H_2O$. Hydrotalcite has a structure in which brucite-like layers carry a positive charge owing to the replacement of some divalent magnesium ions by trivalent aluminum ions. These polycation layers alternate with intermediate layers containing carbonate anions and water. The structure of hydrotalcite is comprehensively described in the above-cited literature, eg. by Cavani et al.

Simple hydroxide salts which are built up of polycations and anions located in between are also known. While the above-described mixed hydroxides are built up of heteropolycations, this structure of such compounds comprises isopolycations. An example is hydrozincite (basic zinc carbonate) whose structure has been determined by Ghose (S. Ghose, "The crystal structure of hydrozincite, $Zn_5(OH)_6(CO_3)_2$," Acta Cryst. 17 (1964) 1051–1057). Compounds of this class can likewise serve as starting materials for alkoxylation catalysts.

On heating the mixed hydroxides, the solvent located between the polycations, usually water of crystallization, is first given off at up to about 200° C. At higher temperatures, for instance on calcination at 500° C., the polycations are degraded with destruction of the structure and the anion may also be decomposed. The calcination is, if not carried out at excessively high temperatures, reversible (known as the "memory effect").

Mixed hydroxides can be prepared relatively simply in the laboratory. In addition, a number of these compounds occur naturally as minerals; examples of these are:

Hydrotalcite $[Mg_6Al_2(OH)_{16}]CO_3 \cdot 4H_2O$
Tacovite $[Ni_6Al_2(OH)_6]CO_3 \cdot 4H_2O$
Hydrocalumite $[Ca_2Al(OH)_6]OH \cdot 6H_2O$
Magaldrate $[Mg_{10}Al_5(OH)_{31}](SO_4)_2 \cdot mH_2O$
Pyroaurite $[Mg_6Fe_2(OH)_{16}]CO_3 \cdot 4.5H_2O$
Ettringite $[Ca_6Al_2(OH)_{12}](SO_4)_3 \cdot 26H_2O$ The synthesis of a mixed hydroxide in the laboratory is generally carried out by precipitation, with a solution containing the cations in dissolved form is combined with a second alkaline solution containing the anion(s) in dissolved form. The exact way in which this precipitation is carried out (pH, temperature, ageing of the precipitate) can have an influence on the chemical composition of the precipitated compound and/or its crystallite morphology.

For the alkoxylation process of the present invention, preference is given to those mixed hydroxides of the general formula I in which M(II) is magnesium, M(III) is aluminum and A is carbonate. Particularly suitable is naturally occurring or synthetically prepared hydrotalcite.

The following classes of substances are suitable for the modification according to the present invention ("hydrophobicization") of the mixed hydroxides described:

(a) aromatic or heteroaromatic mono -or polycarboxylic acids, in particular mono- or dicarboxylic acids, or their salts, especially benzenemonocarboxylic or benzenedicarboxylic acids in which the benzene ring can be additionally substituted by one to three $C_1$–$C_4$-alkyl groups, eg. benzoic acid, p-, m- or p-methylbenzoic acid, p-tert-butylbenzoic acid, p-iso-propylbenzoic acid, p-ethylbenzoic acid, phthalic acid, isophthalic acid, terephthalic acid, pyridinemonocarboxylic and pyridinedicarboxylic acids and also the sodium, potassium and ammonium salts of these;

(b) aliphatic mono-or polycarboxylic acids, in particular mono- or dicarboxylic acids, or their salts having an isocyclic or heterocyclic ring in the side chain, eg. phenyl-$C_2$–$C_4$-alkanoic acids such as phenylacetic acid, 3-phenylpropionic acid or 4-phenylbuteric acid, cyclopentanecarboxylic acid, cyclohexyl-$C_2$–$C_4$-alkanoic acids such as cyclohexylacetic acid, 3-(cyclohexyl)propionic acid or 4-(cyclohexyl)buteric acid, cinnamic acid, o- or p-chlorocinnamic acid, pyridylacetic acids and the sodium, potassium and ammonium salts of these;

(c) monoesters of aliphatic and aromatic dicarboxylic acids and their salts, preferably $C_1$–$C_{18}$-alkyl monoesters of phthalic acid, hexahydrophthalic acid, maleic acid or terephthalic acid, eg. monomethyl, monoethyl or monobutyl esters of phthalic acid or terephthalic acid;

(d) aliphatic and especially alicyclic and aromatic carboxylic anhydrides, eg. maleic anhydride, phthalic anhydride or hexahydrophthalic anhydride;

(e) aliphatic or aromatic sulfonic acids and their salts, eg. methanesulfonic acid, benzenesulfonic acid, p-toluenesulfonic acid, p-dodecylbenzenesulfonic acid, naphthalenesulfonic acids, naphtholsulfonic acids and the sodium, potassium and ammonium salts of these;

(f) $C_8$–$C_{18}$-alkyl sulfates, in particular alkali metal $C_8$–$C_{18}$-alkyl sulfates, eg. sodium or potassium decyl sulfate or sodium or potassium dodecyl sulfate;

(g) long-chain paraffins, in particular $C_8$–$C_{50}$-n-alkanes, especially $C_{10}$–$C_{30}$-n-alkanes such as n-decan or n-dodecane;

(h) polyetherols or polyether polyols, ie. monohydric alcohols having ether-oxygen bridges (polyetherols, polyalkylene glycol monoethers or esters) or polyhydric alcohols having ether-oxygen bridges (polyether polyols), in particular alkoxylated $C_1$–$C_{30}$-alcohols, alkoxylated $C_1$–$C_{30}$-carboxylic acids of aliphatic or aromatic structure or alkoxylated $C_6$–$C_{30}$-phenols, where from 1 to 50 mol, especially from 2 to 30 mol, of a $C_2$–$C_4$-alkylene oxide or a mixture thereof which in the alkoxylated product leads to a random mixture or preferably a blocking of the various alkylene oxide units are used per mole of hydroxyl group; some of the additives (h) are structurally identical with the products obtained in the alkoxylation according to the present invention of compounds having active hydrogen atoms using the correspondingly additive-treated mixed hydroxides I or II;

(j) alcohols or phenols, which are not built in between the layers of the mixed hydroxide I or II (if this mixed hydroxide has a layer structure), in particular aliphatic or cycloaliphatic $C_1$–$C_{30}$-alcohols or $C_6$–$C_{30}$-phenols, especially n-alkanols (fatty alcohols) having from 9 to 18 carbon atoms, eg. n-decanol, n-dodecanol, n-tetradecanol, n-hexadecanol or n-octadecanol; some of the additives (j) are structurally identical with the compounds having active hydrogen atoms, such as the compounds III, used as starting materials in the alkoxylation of the present invention using the correspondingly additive-treated mixed hydroxides I or II.

It is also possible to use mixtures of said additives from one of the classes (a) to (j) or from different classes.

The monoesters (c) can be advantageously obtained by reacting the corresponding carboxylic anhydrides, for example the anhydrides (d), with alcohols such as $C_1$–$C_{18}$-alkanols. It is also possible to use mixtures as alcohol component. Suitable anhydride components are, for example, phthalic anhydride, hexahydrophthalic anhydride or maleic anhydride. It is here also possible to use the alcohol component in excess, so that it simultaneously serves as solvent in the modification of the mixed hydroxides. If an alcohol serves as hydrogen-active compound in the alkoxylation, it is best to select this alcohol for the reaction with anhydrides, so that complicated filtration and drying can be omitted.

In a preferred embodiment, the alkoxylation process of the present invention makes use of a mixed hydroxide I or II containing as additives benzenemonocarboxylic or benzenedicarboxylic acids in which the benzene ring can be additionally substituted by from one to three $C_1$–$C_4$-alkyl groups, phenyl-$C_2$–$C_4$-alkanoic acids, cyclohexanecarboxylic acid, cyclohexyl-$C_2$–$C_4$-alkanoic acids, $C_1$–$C_{18}$-alkyl monoesters of phthalic acid, hexahydrophthalic acid, maleic acid or terephthalic acid, maleic anhydride, phthalic anhydride, hexahydrophthalic anhydride, benzenesulfonic acid, p-toluenesulfonic acid, p-dodecylbenzenesulfonic acid, alkali metal dodecyl sulfates, n-dodecane, n-alkanols having from 9 to 18 carbon atoms or salts of the acids specified.

Very particularly preferred additives are benzoic acid and its alkali metal salts because of the excellent properties as alkoxylation catalysts and the good economics of these compounds, ie. their ready and inexpensive availability.

The molar ratio of the additives (a) to (j) to the mixed hydroxides I or II is usually from 0.01:1 to 10:1, especially from 0.05:1 to 5:1, in particular from 0.2:1 to 2:1.

The structure of the mixed hydroxides is essentially retained after the modification with the additives (a) to (j); in particular, the polycations remain essentially unchanged. The distances of the polycations from one another can be changed to a greater or lesser extent in the modification. In some cases, the additives are present after the modification in neutral or anionic form between the polycations of the mixed hydroxides, with them being able to completely or partially displace the anions located there. In certain cases, the modification of the mixed hydroxides can also be regarded as a type of replacement of the anions originally present by additive anions or anions formed from the additive. The intercalation of the additives between the polycations of the mixed hydroxides generally becomes evident in an increase in the distance between the polycations and can be confirmed by X-ray diffraction.

Such a modification can be carried out for the purposes of hydrophobicization, changing the dispersibility, changing the catalytic properties and/or changing the theological properties of the mixed hydroxides. In other cases, the modification results merely in a coating of the surface of the mixed hydroxides, with the spacing of the polycations remaining unchanged. Such a surface coating can, for example, also serve to hydrophobicize the mixed hydroxides.

Compounds having active hydrogen atoms which can be used are all compounds which have one or more acid hydrogen atoms which can react with alkylene oxides. Particular mention may here be made of alcohols, phenols, carbohydrates, carboxylic acids, carboxamides, amines and mercaptans which are represented by the general formula III

where R is a usual hydrocarbon radical which can also contain hereto atoms and bear further functional groups, Y is O, S, NH or NR and k is 1, 2 or 3.

Depending on the value of k, the radicals R can be monovalent, divalent or trivalent. Preference is given to monovalent and divalent radicals, the most important are monovalent radicals.

Radicals R deserving special mention are:

straight-chain or branched $C_1$–$C_{30}$-alkyl groups and $C_3$–$C_{30}$-alkenyl groups which can be interrupted by one or more non-adjacent oxygen atoms and can bear additional hydroxyl groups, eg. methyl, ethyl, n-propyl, iso-propyl, n-butyl, 2-ethylhexyl, n-octyl, iso-nonyl, n-decyl, n-dodecyl, iso-tridecyl, myristyl, cetyl, stearyl, eicosyl, 2-propenyl, oleyl, linoleyl, linolenyl, 2-methoxyethyl, 2-ethoxyethyl, 2-butoxyethyl, 4-methoxybutyl, 4-(4'-methoxybutyloxy)butyl, 2-hydroxyethyl or 4-hydroxybutyl;

$C_1$–$C_{30}$-acyl groups which can additionally bear hydroxyl groups, eg. formyl, acetyl, propionyl, butyryl, valeryl, decanoyl, lauroyl, myristoyl, palmitoyl, stearoyl or lactyl;

monovalent carbohydrate radicals of monosaccharides or disaccharides when Y=O, eg. radicals of glucose, mannose, fructose, sucrose, lactose or maltose;

aryl groups having a total of from 6 to 20 carbon atoms, which can be additionally substituted by $C_1$–$C_4$-alkyl groups, hydroxyl groups, $C_1$–$C_4$-alkoxy groups and amino groups, eg. phenyl, tolyl, xylyl, hydroxyphenyl, methoxyphenyl, aminophenyl or naphthyl;

arylcarbonyl groups having a total of from 7 to 21 carbon atoms, which can be additionally substituted by $C_1$–$C_4$-alkyl groups, hydroxyl groups, $C_1$–$C_4$-alkoxy groups and amino groups, eg. benzoyl;

divalent radicals derived, for example when Y=O, from diols, dihydroxyaromatics or bisphenols, such as 1,2-ethylene, 1,3-propylene, 1,4-butylene, phenylene or the radical of bisphenol A;

trivalent radicals derived, for example when Y=O, from triols such as glycerol;

polyvalent radicals derived, in particular, from polyols (Y=O), eg. pentaerythritol, or from carbohydrates.

In a preferred embodiment, the hydrogen-active compounds III used are $C_1$–$C_{30}$-alkanols and $C_3$–$C_{30}$-alkenols, in particular $C_8$–$C_{30}$-alkanols and $C_8$–$C_{30}$-alkenols (fatty alcohols).

Suitable $C_2$–$C_4$-alkylene oxides are especially 1,2-propylene oxide, 1,2-butylene oxide, 2,3-butylene oxide and in particular ethylene oxide.

The modified mixed hydroxides described are generally used in the alkoxylation reactions in amounts of from 0.1 to 5% by weight, preferably from 0.15 to 2% by weight, particularly preferably from 0.2 to 0.8% by weight, based on the weight of the compounds having active hydrogen atoms.

The alkoxylation reactions are usually carried out at from 80° to 230° C., preferably at from 100° to 200° C., particularly preferably at from 160° to 180° C. The reaction is generally carried out under pressure, for example in an autoclave at from 2 to 10 bar, in particular from 3 to 7 bar. The reaction is advantageously carried out without solvent, but an inert solvent can be added.

Some of the mixed hydroxides I and II are new compounds. The present invention therefore also provides mixed hydroxides built up of polycations and having the general formula Ia or IIa

(Ia)

(IIa)

where
M(II) is at least one divalent metal ion,
M(III) is at least one trivalent metal ion,
A is at least one inorganic anion and
L is an organic solvent or water,
n is the valence of the inorganic anion A or in the case of a plurality of anions A is their mean valence and
x can assume a value of from 0.1 to 0.5 and
m can assume a value of from 0 to 10,
which have been modified with (a) aromatic or heteroaromatic mono- or polycarboxylic acids or their salts,
(b) aliphatic mono- or polycarboxylic acids or their salts having an isocyclic or heterocyclic ring in the side chain,
(c) monoesters of dicarboxylic acids or their salts,
(d) carboxylic anhydrides,
(e) aliphatic or aromatic sulfonic acids or their salts,
(f) $C_8$–$C_{18}$-alkyl sulfates,
(g) long-chain paraffins,
(h) polyetherols or polyether polyols or
(j) alcohols or phenols, which are not built in between the layers of the mixed hydroxide Ia or IIa, as additives, with the exception of benzoic acid and its salts in the case of a lithium-aluminum mixed hydroxide having a layer structure, with the exception of terephthalic acid, p-toluenesulfonic acid, 2-naphthol-6-sulfonic acid, p- and o-chlorocinnamic acid and the corresponding salts and of n-dodecyl sulfate in the case of magnesium-aluminum mixed hydroxides having a layer structure, and also with the exception of phthalic acid, isophthalic acid, terephthalic acid and pyridinedicarboxylic acids in the case of calcium-aluminum mixed hydroxides.

The literature reference P. K. Dutta and M. Puri, J. Phys. Chem. 1989, 93, 376–381 (4) discloses a lithium-aluminum mixed hydroxide having a layer structure and containing intercalated benzoate anions.

K. Chibwe and W. Jones in the literature reference J. Chem. Soc., Chem. Commun. 1989, 926–927 (5) describe synthetic hydrotalcite containing intercalated sodium dodecyl sulfate and p-toluenesulfonic acid.

The literature reference K. Chibwe, J. B. Valim and W. Jones, Prep. Am. Chem. Soc. 34 (1989) 507–510 (6) discloses magnesium-aluminum mixed hydroxides having a layer structure and containing intercalated terephthalic acid, p-toluenesulfonic acid, 2-naphthol-6-sulfonic acid, p- or o-chlorocinnamic acid and n-dodecyl sulfate.

In all three literature references (4) to (6), only the anion-exchange properties of these mixed hydroxides are studied.

DE-A 40 02 988 (7) and DE-A 41 06 404 (8) disclose calcium-aluminum mixed hydroxides which, inter alia, are modified with phthalic acid, isophthalic acid, terephthalic acid or pyridinecarboxylic acids. These compounds are recommended as stabilizers for halogen-containing thermoplastic resins such as PVC.

The preparation of the mixed hydroxides Ia and IIa of the present invention, but also the remaining mixed hydroxides I and II, ie. the modification using the additives (a) to (j), can be advantageously carried out in three different ways:

(i) the compounds Ia or IIa are directly synthesized ("in situ") by precipitation under alkaline conditions from aqueous solutions of M(II) and M(III) salts or aqueous solutions of lithium and aluminum salts in the presence of the additives (a) to (j);

(ii) the unmodified mixed hydroxides are reacted with the additives (a) to (j) in the presence or absence of a solvent at from 0° to 200° C.;

(iii) the unmodified mixed hydroxides are heated to >200° C., with the temperature selected being able to be no higher than that which allows the mixed hydroxide to subsequently return completely to the original crystal structure, the mixed hydroxide thus treated is reacted with the additives (a) to (j) and is subsequently, if desired, further treated with water.

In the case of (ii), the reaction is generally carried out by mixing the components in a suitable apparatus, eg. a stirred reactor, mixer, kneader or a ball mill, preferably at slightly elevated temperature, for instance from 60° to 200° C. The reaction is usually carried out at pressures of from 0.1 to 50 bar, preferably from 0.5 to 20 bar. If a solvent is to be present, solvents which have been found to be useful for this purpose are water, acetone or an alcohol such as methanol, ethanol or isopropanol. The reaction can be followed by further treatment with solvent and/or drying.

In the case of (iii), the reaction is generally carried out by mixing the components in a suitable apparatus, eg. a mixer, kneader or a ball mill at greatly elevated temperature, for instance from 250° to 550° C. The reaction can be followed by further treatment with solvent and/or drying. The thermal treatment first destroys, at least partially, the structure of the mixed hydroxide. After the treatment with the additive, the original structure of the mixed hydroxide is regained, particularly when further treatment with water takes place.

The mixed hydroxides I and II modified with the additives (a) to (j) are very useful for the alkoxylation of compounds having active hydrogen atoms. They have the advantage that they have a high selectivity and a high reactivity and thus the reaction and cycle times in the alkoxylation are very short. In addition, the by-product spectrum is very small, in particular low polyalkylene glycol contents are obtained. The alkoxylation products produced thus have a very narrow homologue distribution. Such alcohol alkoxylates, particularly alcohol ethoxylates, have advantages in use compared with the products having a broader distribution, usually prepared using NaOH, KOH or sodium methoxide. Thus, they have, for example, lower pour points, lower surface tension, better water solubility and, as a result of a lowering of the free alcohol content (unalkoxylated starting compound), a better odor. The advantage of a narrower homologue distribution is also clearly apparent in comparison with the mixed hydroxides which are modified with aliphatic mono- or dicarboxylic acids and are known from the prior art.

The modified mixed hydroxides I and II have the advantage in the alkoxylation reaction that they are more readily dispersible in the reaction medium, eg. long-chain fatty alcohols, but after the reaction can be easily removed again by filtration. If they do not interfere with further use of the products, the mixed hydroxides can remain in the product where they can effect an alteration of its rheological properties.

After the alkoxylation is complete, the modified mixed hydroxides I and II can in principle be reused after they have been separated from the reaction mixture in an appropriate manner.

EXAMPLES

Preparation of Mixed Hydroxides Modified with Additives

The modified mixed hydroxides shown in Table 1 as Examples 1 to 13 and Comparative Examples 14 and 15 were prepared according to one of the preparative procedures A to E.

TABLE 1

| Ex. No. | Mixed hydroxide | Additive | Amount of additive [g] | Preparative procedure |
|---|---|---|---|---|
| 1 | Hydrotalcite | Benzoic acid | 150 | A |
| 2 | Hydrotalcite | p-tert.-Butyl-benzoic acid | 200 | A |
| 3 | Hydrotalcite | Benzoic acid | 80 | B |
| 4 | Hydrotalcite | Benzoic acid | 40 | B |
| 5 | Hydrotalcite | Benzoic acid | 20 | B |
| 6 | Hydrotalcite | p-tert.-Butyl-benzoic acid | 100 | B |
| 7 | Zinc-aluminum mixed hydroxide | Benzoic acid | 80 | B |
| 8 | Hydrotalcite | Phthalic anhydride | 75 | C |
| 9 | Hydrotalcite | Benzoic acid | 80 | C |
| 10 | Hydrotalcite | Benzoic acid | 150 | D |
| 11 | Hydrotalcite | p-tert.-Butyl-benzoic acid | 200 | D |
| 12 | Hydrotalcite | p-Methylbenzoic acid | 200 | D |
| 13 | Calcium-aluminum mixed hydroxide | Phthalic acid | 33 | E |
| for comparison: | | | | |
| 14 | Hydrotalcite | Lauric acid | 250 | A |
| 15 | Hydrotalcite | Lauric acid | 200 | D |

The hydrotalcite used was a commercial material.
The zinc-aluminum mixed hydroxide of Example 7 was prepared as follows:

A solution of 0.2 mol of aluminum nitrate and 0.7 mol of zinc nitrate in 1 liter of water and a solution of 1 mol of sodium carbonate in 1 liter of water were added simultaneously at 80° C. to 500 ml of 2 molar sodium nitrate solution while stirring. The two solutions were run in over a period of 60 minutes and the feed was metered in such a way that the mixture always had a pH of 6.5. After the precipitation was complete, tile mixture was stirred for a further 30 minutes at 80° C., with the pH again being kept constant. The precipitate was filtered off, washed free of nitrate and dried at 100° C. Elemental analysis indicated the following approximate chemical composition of the zinc-aluminum mixed hydroxide: $[Zn_6Al_2(OH)_{16}]CO_3 \cdot mH_2O$.

Preparative Procedure A:

300 g of mixed hydroxide together with a saturated solution of the additive in isopropanol were placed in a stirred vessel. The mixture was refluxed while stirring for two hours. The solid phase was subsequently filtered off, washed with pure isopropanol and dried at 110° C.

Preparative Procedure B:

150 g of mixed hydroxide together with the additive were placed in a kneader. The mixture was kneaded for two hours at 80° C.

Preparative Procedure C:

150 g of mixed hydroxide together with the additive and 100 g of dodecanol as solvent were placed in a kneader. The mixture was kneaded for two hours at 80° C.

Preparative Procedure D:

300 g of mixed hydroxide were heated for two hours at 500° C. and subsequently placed in a stirred vessel together with a saturated solution of the additive in water. The mixture was heated at 80° C. for two hours while stirring. The solid was subsequently filtered off, washed with pure water and dried at 110° C.

Preparative Procedure E:

22 g of calcium hydroxide together with 8 g of sodium hydroxide and 16 g of aluminum hydroxide were suspended in 500 ml of water and heated to 80° C. A solution of 33 g of phthalic acid in 400 ml of water was subsequently added at this temperature while stirring. The suspension was stirred for a further 2 hours at 80° C. The solid was filtered off, washed with water and dried at 110° C.

In addition, the following modified mixed hydroxides of the present invention were prepared from commercial hydrotalcite:

Example 16

(hydrotalcite+benzoic acid)

10 g of dried hydrotalcite together with 4 g of benzoic acid were heated to 150° C. in an autoclave while stirring. The pressure rose by about 5 bar. The autoclave was vented and the mixture was treated at 150° C. for a further four hours. The product was subsequently treated at 200° C. for one hour in a drying oven.

Example 17

(hydrotalcite+n-decanol)

10 g of dried hydrotalcite were dispersed in 200 g of n-decanol at 60° C. for 30 minutes by means of a high-speed mixer. The solid was subsequently filtered off.

Example 18

(hydrotalcite+benzoic acid)

900 g of dried hydrotalcite together with 90 g of benzoic acid were treated at 80° C. for four hours in a 5 liter ploughshare mixer running at 140 rpm. The product was subsequently treated at 150° C. for one hour in a drying oven.

Ethoxylations Using the Modified Mixed Hydroxides

General procedure for the ethoxylation:

1 mol of dodecanol (186 g) and 0.5% by weight of catalyst from Examples 11 to 12 or Comparative Examples 14 or 15 were placed in a steel autoclave and dewatered at 120° C. for 1 hour under reduced pressure. The temperature was subsequently raised to 170° C. and 5 mol of ethylene oxide (220 g) were injected at this temperature, the ethylene oxide feed being regulated in such a way that the internal pressure in the autoclave did not rise above 6 bar. After the feeding in of ethylene oxide was complete, the mixture was stirred further at 170° C. until the pressure was constant. The product obtained was filtered hot.

Table 2 gives the reaction times, polyethylene glycol contents (based on PEG 400), residual alcohol contents and homologue distributions. The latter were determined by means of gas chromatography and are given in percent by area.

It can be seen from the examples that, in comparison with the prior art (Comparative Examples 14 and 15), an improvement was achieved in respect of polyethylene glycol content and the maximum in the homologue distribution. The residual alcohol contents are in many cases lower than in the comparative examples.

TABLE 2

| Ex. No. | Reaction time [h] | Polyethylene glycol content [% by wt.] | Residual alcohol content [% by wt.] | $E_1$ | $E_2$ | $E_3$ | $E_4$ | $E_5$ | $E_6$ | $E_7$ | $E_8$ | $E_9$ | $E_{10}$ | $E_{11}$ |
|---|---|---|---|---|---|---|---|---|---|---|---|---|---|---|
| 1 | 2 | 1.7 | 0.5 | 1.1 | 2.8 | 10.1 | 21.2 | 29.4 | 20.1 | 9.0 | 4.2 | 1.0 | 0.6 | 0 |
| 2 | 1.5 | 1.4 | 0.4 | 0.9 | 2.3 | 9.2 | 19.8 | 31.3 | 21.4 | 9.5 | 3.8 | 0.9 | 0.5 | 0 |
| 3 | 2 | 1.9 | 0.5 | 1.2 | 2.8 | 10.2 | 21.5 | 29.0 | 20.2 | 9.2 | 4.2 | 1.1 | 0.6 | 0 |
| 4 | 2 | 2.0 | 0.7 | 1.3 | 2.7 | 10.0 | 21.7 | 29.5 | 19.9 | 8.8 | 3.5 | 1.5 | 0.4 | 0 |
| 5 | 2.25 | 2.0 | 0.8 | 1.2 | 2.6 | 11.0 | 20.9 | 29.3 | 19.5 | 9.0 | 3.6 | 1.7 | 0.4 | 0 |
| 6 | 2 | 1.8 | 0.3 | 0.7 | 2.2 | 9.0 | 21.2 | 31.9 | 20.8 | 8.9 | 3.5 | 0.8 | 0.2 | 0 |
| 7 | 2 | 1.5 | 0.6 | 1.2 | 3.0 | 9.9 | 20.9 | 29.0 | 20.4 | 9.1 | 4.2 | 1.1 | 0.5 | 0 |
| 8 | 3.5 | 1.5 | 0.5 | 0.8 | 2.0 | 10.0 | 19.9 | 29.9 | 22.4 | 9.5 | 3.5 | 1.0 | 0.5 | 0 |
| 9 | 1 | 1.0 | 0.5 | 1.1 | 2.9 | 10.2 | 21.7 | 29.0 | 20.0 | 9.0 | 4.0 | 1.0 | 0.6 | 0 |
| 10 | 1.5 | 1.1 | 0.5 | 1.2 | 3.8 | 12.0 | 20.0 | 26.5 | 18.5 | 9.5 | 4.7 | 2.0 | 1.0 | 0.3 |
| 11 | 1 | 0.8 | 0.3 | 1.0 | 2.9 | 10.0 | 20.5 | 30.1 | 20.9 | 9.3 | 4.0 | 1.0 | 0.3 | 0 |
| 12 | 1 | 1.1 | 0.3 | 1.1 | 2.8 | 10.4 | 20.9 | 28.0 | 18.7 | 10.0 | 5.0 | 1.9 | 0.6 | 0.1 |
| for comparison: | | | | | | | | | | | | | | |
| 14 | 2.5 | 2.2 | 0.7 | 1.7 | 3.9 | 12.2 | 23.0 | 2.50 | 20.1 | 7.5 | 3.8 | 1.3 | 0.6 | 0.2 |
| 15 | 1.5 | 1.7 | 0.5 | 1.7 | 5.3 | 13.0 | 21.3 | 26.0 | 19.0 | 7.5 | 3.0 | 1.2 | 0.4 | 0.1 |

We claim:

1. A process for preparing an alkoxylation product comprising reacting a compound having active hydrogen atoms with at least one of $C_2$–$C_4$-alkylene oxides in the presence of a mixed hydroxide built up of polycations and modified with one or more additives and having the general formula I or II $$[M(II)_{1-x}M(III)_x(OH)_2]A_{x/n} \cdot m\, L \qquad (I)$$

$$[LiAl_2(OH)_6]A_{1/n} \cdot m\, L \qquad (II)$$

where
M(II) is at least one divalent metal ion,
M(III) is at least one trivalent metal ion,
A is at least one inorganic anion and
L is an organic solvent or water,
n is the valence of the inorganic anion A or in the case of a plurality of anions A is their mean valence and
x can assume a value of from 0.1 to 0.5 and
m can assume a value of from 0 to 10,
as alkoxylation catalyst, wherein said one or more additives is at least one selected from the group consisting of (a) aromatic or heteroaromatic mono-or polycarboxylic acids or their salts, (b) aliphatic monocarboxylic acids or their salts from the group phenyl-$C_2$–$C_4$-alkanoic acids, cyclopentanecarboxylic acid, cyclohexanecarboxylic acid, cyclohexyl-$C_2$–$C_4$-alkanoic acids, cinnamic acid, o- or p-chlorocinnamic acid and pyridylacetic acids, (c) monoesters of dicarboxylic acids or their salts, (d) carboxylic anhydrides, (e) aliphatic or aromatic sulfonic acids or their salts, (f) $C_8$–$C_{18}$-alkyl sulfates, (g) $C_8$–$C_{50}$-n-alkanes, (h) polyetherols or polyether polyols, and (j) alcohols or phenols,which are not build in between the layers of the mixed hydroxide I or II.

2. A process for preparing alkoxylation products as claimed in claim 1 in the presence of a mixed hydroxide of the general formula I in which M(II) is magnesium, M(III) is aluminum and A is carbonate.

3. A process for preparing alkoxylation products as claimed in claim 1, wherein the mixed hydroxide I or II contains as additives benzenemonocarboxylic or benzenedicarboxylic acids, in which the benzene ring can be additionally substituted by from one to three $C_1$–$C_4$-alkyl groups, phenyl-$C_2$–$C_4$-alkanoic acids, cyclohexanecarboxylic acid, cyclohexyl-$C_2$–$C_4$-alkanoic acids, $C_1$–$C_{18}$-alkylmonoesters of phthalic acid, hexahydrophthalic acid, maleic acid or terephthalic acid, maleic anhydride, phthalic anhydride, hexahydrophthalic anhydride, benzenesulfonic acid, p-toluenesulfonic acid, p-dodecylbenzenesulfonic acid, alkali metal dodecyl sulfates, n-dodecane, n-alkanols having from 9 to 18 carbon atoms or salts of the acids specified.

4. A process for preparing alkoxylation products as claimed in claim 1, wherein the additives (a) to (j) are used in a molar ratio to the mixed hydroxides I or II of from 0.01:1 to 10:1.

5. A process for preparing alkoxylation products as claimed in claim 1 by reaction of $C_1$–$C_{30}$-alkanols or $C_3$–$C_{30}$-alkenols as compounds having active hydrogen atoms.

6. A process for preparing alkoxylation products as claimed in claim 1, wherein the mixed hydroxides I or II are used in amounts of from 0.1 to 5% by weight, based on the weight of the compounds having active hydrogen atoms.

7. A process for preparing alkoxylation products as claimed in claim 1, wherein the reaction is carried out at from 80° to 230° C. and pressures of from 2 to 10 bar.

8. A mixed hydroxide built up of polycations and having the general formula Ia or IIa $$[M(II)_{1-x}M(III)_x(OH)_2]A_{x/n} \cdot m\, L \qquad (Ia)$$

$$[LiAl_2(OH)_6]A_{1/n} \cdot m\, L \qquad (IIa)$$

where
M(II) is at least one divalent metal ion,
M(III) is at least one trivalent metal ion,
A is a least one inorganic anion and
L is an organic solvent or water,
n is the valence of the inorganic anion A or in the case of a plurality of anions A is their mean valence and
x can assume a value of from 0.1 to 0.5 and
m can assume a value of from 0 to 10,
which has been modified with at least one additive selected from the group consisting of (a) aromatic or heteroaromatic mono-or polycarboxylic acids or their salts, (b) aliphatic monocarboxylic acids or their salts from the group phenyl-$C_2$-$C_4$-alkanoic acids, cyclopentanecarboxylic acid, cyclohexanecarboxylic acid, cyclohexyl-$C_2$-$C_4$-alkanoic acids, cinnamic acid, o- or p-chlorocinnamic acid and pyridylacetic acids, (c) monoesters of dicarboxylic acids or their salts, (d) maleic anhydride, phthalic anhydride or hexahydrophthalic anhydride, (e) aliphatic sulfonic acids or their salts, (f) $C_8$–$C_{18}$-alkyl sulfates, (g) $C_8$–$C_{50}$-n-alkanes, and (j) alcohols or phenols, which are not built in between the layers of the mixed hydroxide I or II, with the exception of benzoic acid and its salts in the case of a lithium-aluminum mixed hydroxide having a layer structure, with the exception of terephthalic acid, p- and o-chlorocinnamic acid and the corresponding salts and of n-dodecyl sulfate in the case of magnesium-aluminum mixed hydroxides having a layer structure, and also with the exception of phthalic acid, isophthalic acid, terephthalic acid and pyridinedicarboxylic acids in the case of calcium-aluminum mixed hydroxides.

9. A process for preparing a mixed hydroxide Ia or IIa as claimed in claim 8, which comprises precipitating the compounds Ia or IIa under alkaline conditions from aqueous solutions of M(II) and M(III) salts or aqueous solutions of lithium and aluminum salts in the presence of said at least one additive.

10. A process for preparing a mixed hydroxide Ia or IIa as claimed in claim 8, which comprises reacting the unmodified mixed hydroxide with said at least one additive in the presence or absence of a solvent at from 0° to 200° C.

11. A process for preparing a mixed hydroxide Ia and or IIa as claimed in claim 8, which comprises heating the unmodified mixed hydroxide to >200° C., with the temperature selected being able to be no higher than that which allows the mixed hydroxide to subsequently return completely to the original crystal structure, reacting the mixed hydroxide thus treated with said at least one additive and subsequently, if desired, further treating it with water.

* * * * *